United States Patent [19]
Ishibashi

[11] Patent Number: 6,033,657
[45] Date of Patent: Mar. 7, 2000

[54] MASS PRODUCTION AND LONG-TERM PRESERVATION OF FUNGIVOROUS NEMATODES AND USES THEREOF

[76] Inventor: Nobuyoshi Ishibashi, 1090-3, Chifu, Kinryu-Machi, Saga City, Saga Pref., Japan

[21] Appl. No.: 09/075,940

[22] Filed: May 12, 1998

Related U.S. Application Data

[62] Division of application No. 08/977,626, Nov. 25, 1997.

[30] Foreign Application Priority Data

Feb. 4, 1997 [JP] Japan .................................. 9-21245

[51] Int. Cl.[7] .............................. A01K 63/00; C12N 1/04
[52] U.S. Cl. ........................ 424/93.1; 424/93.7; 435/260
[58] Field of Search .................................. 424/93.1, 93.7; 435/260

[56] References Cited

U.S. PATENT DOCUMENTS 5,183,950  2/1993  Popiel et al. ................................ 800/2
5,554,533  9/1996  Bedding et al. .

FOREIGN PATENT DOCUMENTS

WO95/02958  2/1995  WIPO .

OTHER PUBLICATIONS

Simons et al., "The ability of *Neoaplectana carpocapsae* (Steinernematidae:nematode) to survive extended periods of desiccation", Journal of Invertebrate Pathology, 1973, vol.22, pp. 228–230.

Evans et al., In: Nematodes as Biological Models. Academic Press. 1980, vol.2, pp. 193–211.

Crowe et al., "Anhydrobiosis inNematodes: permeability during rehydration", J. Exp. Zool., 1979, 207, pp. 431–438.

Townshend, Fungus Hosts of *Aphelenchus Avenae Bastian*, and *Bursaphelechus Fungivorus* Franklun & Hooper, 1962 and their attractiveness to these nematode species, Canadian Journal of Microbiology, Mar. 24, 1964, pp. 727–737.

Choi et al. "Preparation of Five *Aphelechus avenae* Isolates on Six Species of Fungi and Five Substrates" Japan Journal of Nematology, vol. 19, Dec. 1989, pp. 13–17.

Ishibashi et al. "Biological Control of Soil Pests by Mixed Application of Entomophathogenic and Fungivorous Nematodes" Journal of Nematology 23(2) 1991 pp. 175–181.

Ishibashi "Integrated Control of Insect Pests by *Steinernema carpocapsae* " ed. Bedding et al., CSIRO, East Melbourne, Australia, pp. 105–113.

Ishibashi "Detection of Beneficial Nematodes in Japan and Systematized Nematode Application" Research Project on Biological Control Supported by Grant–in–Aid for Developmental Scientific Research, Ministry of Education, Culture and Science, Japan, Mar. 1993.

*Primary Examiner*—Sandra E. Saucier
*Assistant Examiner*—Vera Afremova
*Attorney, Agent, or Firm*—Venable; John W. Schneller; Charles C. Rories

[57] ABSTRACT

A host fungus of a fungivorous nematode is inoculated on a solid medium or an artificial liquid medium containing an industrial vegetable waste or by-product, and then the nematode whose whole body have been sterilized is inoculated and mass-cultivated. Fungivorous ability of the nematode can be kept by subculturing using different host fungus on every culturing stage. The nematodes, when maintained about 10 days in an aerobic condition at 20–25° C. with a relative humidity gradually inclined from high to low and dried to anhydrobiotic conditions, can be preserved for a long time. The nematode can be used for biological control of soil pathogens and soil insect pests.

13 Claims, No Drawings

MASS PRODUCTION AND LONG-TERM PRESERVATION OF FUNGIVOROUS NEMATODES AND USES THEREOF

This application is a divisional of 08/977,626 filed Nov. 25, 1997, now allowed.

BACKGROUND OF THE INVENTION

1. Field of the Invention

The present invention relates to a soil conditioner which prevents agricultural and forest soil-borne diseases and nematode diseases caused by plant-parasitic filamentous fungi and plant-parasitic nematodes, with fungivorous nematodes, i.e., *Aphelenchus avenae*, more particularly, mass production of the fungivorous nematodes with solid media comprising industrial vegetable wastes or artificial liquid media, and long-term preservation and uses thereof.

2. Description of the Prior Art

It is undisputable that chemical pesticides that farming crops have hitherto been depending upon, though they have caused much environmental pollution, are still the main stream of agricultural production means. On the other hand, efforts have been made to spread sustainable agriculture as a task of the 21st century, wherein beneficial viruses, bacteria, fungi, entomopathogenic nematodes, natural enemy insects and so forth have been assiduously studied. However, there is no almighty in the biological means, and those which can control insect pests relatively over a wide range are only entomopathogenic nematodes and BT agents (bacteria). It is furthermore difficult to treat diseases, as no biological materials or means for controlling concurrently more than 2~3 pathogens have been available.

SUMMARY OF THE INVENTION

The fungivorous nematodes represented by *Aphelenchus avenae* (hereinafter referred to as "NEMATODE"), used in the present invention are ubiquitous in the Temperate Zone, and live on soil filamentous fungi. It has been reported that the NEMATODES can be cultured experimentally with 96 species of fungi (Townshend, J. L. (1964) Fungus hosts of *Aphelenchus avenae* Bastian, 1865 and *Bursaphelenchus fungivorous* Franklin and Hooper, 1962 and their attractiveness to these nematode species. Can. J. Microbiol. 10:727–737). Amongst the above, since many species of fungi which are also soil pathogens are included, the studies of biological control of soil-borne diseases with the NEMATODES have been conducted since these 30 years mainly in Europe and America and numbers of experimental results have been reported. In these experiments, the papers reported that the effect in the control was more than 70–80%. However, since the experimental scale was rather small and sterilized soil was used in most experiments, damages due to the NEMATODES themselves were experienced in some cases. Therefore, it has not been put into practice. Further, in some other experiments, since the NEMATODES were not applied in an appropriate period, the efficacy of nematodes in control was unclear. Thus, the reasons why this method has not been put into practice are enumerated as follows:

1. The mass production method has not been established. Therefore, a field test on a large scale which is persuasive enough has never been conducted.
2. When the NEMATODES are serially subcultured with the same fungus, even if the fungus is the best for the propagation of the NEMATODES, the NEMATODES decrease fungivorous ability after several generations until the maintenance of the species becomes almost difficult after a year (Edited by N. Ishibashi (1993), "Detection of Beneficial Nematodes in Japan and Systematized Nematode Application" Report on Study Results P, Test Results A of 1992 Grant-in-aid of Scientific Research, p. 172).
3. When only plant seeds and the NEMATODES are put in sterilized soil, the NEMATODES may be detrimental to the plant, though it depends upon the species of the vegetable. Thus, the NEMATODES cause germination inhibition and have been judged as an injurious nematode (however, in practical fields, the sterilized soil can not exist).
4. It has been known that the NEMATODES survive long in a dry state. However, a technique for maintaining a large quantity of the NEMATODES in such a state has not been developed.
5. The NEMATODES are generally different in host preference, depending on the places of collection (isolates). Thus, a world-wide unified strain has not been established. Therefore, test results were sometimes totally reversed depending on the isolates and investigators. Thus, the usefulness of the NEMATODES as a biological agent for control of soil-borne fungal diseases was rather assessed as deniable.

In the present invention, among the above tasks, important problems were solved from the practical point of view as follows.

The mass production of the NEMATODES that was proposed in the Task 1 (see reason 1 above) is indispensable for putting into practice in a field. According to the first embodiment, the process for achieving such a mass production comprises the sequential steps of: heat-sterilizing a solid medium comprising an industrial vegetable waste of by-product; inoculating a host fungus for NEMATODES to said solid medium; inoculating said NEMATODES whose whole body surface has been sterilized to said solid medium, not before the inoculation of said host fungus; and conducting cultivation of said NEMATODES and fungus. Alternatively, according to the second embodiment, the process of mass production of NEMATODES comprises the sequential steps of: heat-sterilizing an artificial liquid medium comprising a multiporous solid substrate impregnated with a liquid medium containing starch and dextrose or sucrose together with a phosphate buffer saline; inoculating a host fungus for NEMATODES to said artificial liquid medium; inoculating NEMATODES whose whole body surface has been sterilized to said solid medium, not before the inoculation of said host fungus; and conducting incubation of NEMATODES and fungus.

Namely, the process of mass production of the NEMATODES is characterized in that a solid substrate comprising industrial vegetable wastes or by-products, or an artificial liquid medium comprising a porous resin substrate impregrated with a culture medium containing starch and dextrose or sucrose and phosphate buffered saline is heat sterilized, then the above solid substrate or liquid medium is inoculated with a host fungus for the NEMATODES, and the surface of the NEMATODES is sterilized and inoculated concurrently with or after the inoculation of the fungus on the above substrate/medium and then incubated.

The decrease in propagation capacity by the subculture that was raised in the Task 2 (see reason 2 above) is solved by serial stepwise subculturing the NEMATODES with feeds of fungi different in species on every stage and using a non-pathogenic fungus as a feed on the final incubation stage. Namely, this task can be overcome by changing the host fungi. For example, if a laboratory test is commenced with *Botrytis cinerea,* the host fungus is changed, for example, to *Rhizoctonia solani* next, Pythium or Fusarium further next and so forth. Any fungi with which the NEMATODES can be propagative may be applied, but in the final stage of the mass production, it is preferred to incubate with a non-vilulent strain of *Botrytis cinerea* as the host.

The problem of the germination inhibition in the sterilized soil that was raised in the Task 3 (see reason 3 above) will be mainly significant in the course of an experimental or investigative work. It is not so serious a problem in a practical farmland. However, it has been found that even this problem can be solved by appropriately utilizing the NEMATODES. Namely, in the sterilized conditions, if vegetable seeds are inoculated with a large quantity of the NEMATODES (for example, some ten thousand NEMATODES per a cucumber seed), the germination ratio may decrease by 20–30% in some cases. Alternatively, even if it germinates, damaged spots like leafminer's galleries will appear in cotyledons. Though no damages may appear depending upon the species of the vegetable, generally the seeds of Cucurbitaceae are susceptible to the damages. However, if the NEMATODES are inoculated together with pathogenic fungi or other nematodes (for example, entomopathogenic nematodes), such damages never appear at all. Even though damages like leafminer's galleries appear in cotyledons, the NEMATODES do not rise up to the ground level so that no further damages occur. In non-sterilized soil, the NEMATODES do not damage at all. As a matter of fact, since the sterilized soil does not exist naturally, it is not considered necessary to concern the germination inhibition.

Further, if a large quantity of the NEMATODES are applied to soil (the same as the case in entomopathogenic nematodes), the native nematode fauna will be drastically modified. Free-living native nematodes increase and plant-parasitic nematodes decrease in consequence. It is considered that the NEMATODES will also be enticed towards the plant roots where they are swarmed around the tip of the roots, to thereby obstruct the approach or invasion of the plant-parasitic nematodes to the roots. Therefore, if the NEMATODES are applied to prevent the deterioration of the soil biota by application of chemicals, it can suppress the rapid recovery of the nematode pests (Ishibashi, N., and Choi, D-R. (1991) Biological control of soil pests by mixed application of entomopathogenic and fungivorous nematodes. J. Nematol. 23:175–181).

The long-term preservation of the NEMATODES that was proposed in the Task 4, (see reason 4 above) is important in the practice on an agricultural or commercial scale. The long-term preservation of the NEMATODES is relatively easy by comparison with the entomopathogenic nematodes (beneficial nematodes already commercialized and used in the biological control of the insect pests), and can be achieved as follows: namely, the mass-produced NEMATODES are collected to form a lump which is maintained under aerobic conditions at a temperature of 20–25° C. for 8–12 days, with a relative humidity gradually inclined from a high humidity ranging 100–97% to a low humidity ranging 40–25%, whereby the above NEMATODES are dried to an anhydrobiotic condition and preserved. The NEMATODES thus have turned into an anhydrobiosis can survive for a long period of time, even in a humidity of 30% or less.

Namely, the NEMATODES which have turned into a perfect anhydrobiosis after around 20 days are contracted into almost a coiled shape and can be preserved for a year or more in the interior. If they are kept in a low temperature of about 5° C., they can be preserved for 2 years or more. Though the most surviving stage is the fourth-stage juveniles, the NEMATODES on another stage can increase the survivability, if they are in the shape of lump. They should be protected from acari during preservation. However, the hermetical closing of the container for preventing inclusion of acari will put the NEMATODES in a danger of annihilation due to lack of oxygen. Further, a more careful attention should be paid when the NEMATODES are hydrated rather than dehydrated. If the NEMATODES in a dry state are put into water abruptly, some individuals will burst. If the lump of the NEMATODES is large enough, it will be no problem. However, since the lump will collapse with various operations during preservation, it is recommended to put the NEMATODES in a vessel of 100% humidity overnight when they are reconstituted with water.

As to the difference in host preference that was raised in the Task 5, (see reason 5 above) since the classification of nematodes is a descriptive taxology, the same shape is classified in the same species. However, even if classified in the same species, there are many nematodes different in physiology and ecology. The nematodes universally existing all over the world are particularly strong in this tendency. The NEMATODES also are ubiquitous over the world, and the host preference largely depends upon the place of the collection. For example, the NEMATODE isolate from Kyushu is most propagated with feeding *Rhizoctonia solani,* while the NEMATODE isolate from Tohoku District likes Pythium better. Thus, nematodes which are different in host preference are treated as such and such an isolate. If the isolates like those are investigated further minutely, the nematode isolates particularly suited for treating a certain disease will be exploited. Classification on a DNA level is expected in a nation-wide, or world-wide arrangement of isolates ("Search for beneficial nematodes and mass production and systematization of application methods thereof", vide supra). In the present invention, needless to say, it is most preferred that the host preference of the NEMATODES is clarified and a host fungus corresponding thereto is used, or that the NEMATODES which meet the host fungus living in soil is applied.

DESCRIPTION OF THE PREFERRED EMBODIMENTS (Mass-production Method of the Fungivorous Nematodes)
1. Incubation with Industrial Vegetable Waste or By-products.

As to sugar cane strained lees (bagasse), fruit strained lees produced in the manufacturing process of fruit juice (fruit juice strained lees), strained lees produced in the manufacturing process of distilled spirits (distilled spirits strained lees), chaff, bran, brewer's grains, beet pulp, potato chip waste, media after mass-breeding of melon flies, used green tea leaves, used oolong tea leaves, grounds produced in the manufacturing process of instant coffee (coffee grounds), etc., though they can be utilized as stock feeds or fuels, most of them are discarded, and many enterprises are perplexed how to treat them. These vegetables as substrates can cultivate fungi if the temperature and humidity are in preferable conditions. Further, if the fungi are the host, the NEMATODES can be cultured.

All of the fungi grow on the above vegetable substrates, i.e., solid media. However, with one kind of substrate, the fungi much differ in propagation. As the result, the nematodes also much differ in propagation. Even the beet pulp substrate or melon flies mass-bred medium which can well propagate both the fungi and nematodes with only one kind of substrate or medium can be further improved into a better substrate or medium by adding more or less of other substrate thereto. This is because, by mixing a plurality of substrates or media, the substrates or media are provided with a buffer action so that the substrates or media do not increase their pH in the cultivation period of the fungi and nematodes. Particularly, the used tea leaves adsorb the generated ammonia and effectively suppress the pH increase. Accordingly, whatever substrate or medium is prepared, it is recommended that 2–3 kinds of substrates or media are mixed with the used tea leaves.

Basically, since it is necessary that the whole of such solid medium should be provided with vacant spaces therein, vegetable substrates having much vacancy will be employed as a basic substrate. Amongst the currently available vegetable industrial wastes, those can be the basic substrates are the bagasse, beet pulp, chaff, bran, fruit juice strained lees, used tea leaves and potato chip waste. For example, when the bagasse is used as the basic substrate, a preferred formulation is, as dry weight, either 1 part of bagasse, 1 part of fruit juice strained lees and 1 part of used green tea leaves, or 1 part of bagasse, 1 part of potato chip waste and 1 part of used green tea or oolong tea leaves. Alternatively, when the beet pulp is used as the basic substrate, a preferred formulation is: 1 part of beet pulp, 1 part of brewer's grains or fruit juice strained lees and 1 part of used tea leaves. Further, when the chaff is used as the basic substrate, the formulation may be: 1 part of chaff, 1 part of fruit juice strained lees and 1 part of used tea leaves. In the case of the potato chip waste, though it may be used alone, the mixture with the aforementioned used tea leaves is recommended. The water content is preferably 50–60% in any prepared substrates. The pH is most preferred to be kept in the range of 5–6 during the cultivation.

After these solid media are sterilized in an autoclave, fungi which are the hosts of the NEMATODES are inoculated. As to *Rhizoctonia solani* of which hyphae rapidly grow, the hypha suspension and the NEMATODES may be inoculated concurrently. As for *Botrytis cinerea* which grows somewhat slower than *Rhizoctonia solani*, the NEMATODES may be inoculated about 3 days after the inoculation of hyphae. It is necessary to sterilize the surface of the NEMATODES before the inoculation. For example, about 70 NEMATODES are soaked in a 1,000 ppm streptomycin solution for 30 minutes, centrifugally washed with sterilized water for 3 times, and then inoculated on 20g of solid medium (water content: 60%, and dry weight: about 7 g).

The substrate on which the NEMATODES were best propagated was 1 part of beet pulp and 1 part of brewer's grains, which produced about $4 \times 10^6$ NEMATODES after 3 weeks with a feed of *Botxytis cinerea*. Though the beet pulp itself is well worthy as stock feeds, nothing is better than the above mixed substrate for the production of the NEMATODES with a solid medium. With the combination of the most easily procurable fruit juice strained lees, potato chip waste and bagasse, the production of the NEMATODES is $1 \sim 1.5 \times 10^6$. Computing based upon the above, about $150 \sim 200 \times 10^6$ NEMATODES per 1 kg dry substrate can usually be produced (Choi, Dong-Ro, and Ishibashi, Nobuyoshi (1989), Propagation of five *Aphelenchus avenae* isolates on six species of fungi and five substrates. Jpn. J. Nematol. 19:13–17).

However, since 3 kg wet substrate containing 60% of water requires a 10 liter container and occupies a large space for mass production, the production of the nematodes with solid media is not always efficient. Further, during the cultivation, it is required to prevent acari from intrusion. Therefore, a further efficient mass cultivation method is with an artificial liquid medium.

2. Incubation of Host Fungi and Fungivorous Nematodes with an Artificial Liquid Medium This method aims at mass production of the NEMATODES by using a fermentor. In order for the NEMATODE to eat the fungus, since its stylet should be stung perpendicularly to the hyphal tissue, a support for the body of the NEMATODE is required. For this reason, the whole substrate cannot be a liquid. Therefore, a solid substrate required for propagation of the fungus is impregnated with a liquid medium for propagation of fungus.

As mentioned before, since for the mass production of the NEMATODES, an appropriate vacancy is required in the medium, the selection of the substrate is material. Further, since agar is not used, the liquid medium nutrients impregnating the substrate should be slightly richer than the case where the agar is used. The liquid medium is adjusted by phosphate buffered saline so as to keep pH in the range of 5~6 during the incubation. Considering such requirements, an example of the prepared substrate and medium is as follows:

Substrate: spongy materials, for example, multiporous resins such as foamed polyurethanes, microporous (continuous pore) polyvinyl formal resins or the like, or fibrous aggregates such as organic or inorganic fiber linters, woven or nonwoven fabrics, knitted fabrics or the like, rags thereof, animal or vegetable microporous materials, such as sponges, and solid materials having water absorbency and water retention, are applicable. These are cut or aggregated into an appropriate size, sufficiently washed with water and dried, before use.

Liquid medium: agar is removed from the PDA or PSA medium, a phosphate buffered saline is used in lieu of distilled water, and starch and dextrose or sucrose are added as prescribed. The liquid medium is preferred to have pH in the range of 5.2~5.5.

The above substrate, for example, a sponge is impregnated with the above liquid medium, charged in a fermentor, removed excessive water and then subjected to sterilization at about 120° C. for about 60 minutes in an autoclave. Then, a host fungus and the NEMATODES are inoculated on the medium in the fermentor. The fungus and the NEMATODES are inoculated concurrently, or the NEMATODES are inoculated appropriately later than the inoculation of the fungus. For example, in the case where the fungus is *Rhizoctonia solani,* it may be inoculated concurrently with the NEMATODES, and when *Botzytis cinerea* is the host, it may be inoculated about 2 days before the inoculation of the NEMATODES. Alternatively, in the case where a large amount of the NEMATODES to be inoculated are retained on a spongy medium or the like, the spongy medium cut into 4~5 cm cubes in a clean bench may be put directly on the spongy medium in the fermentor container.

It is necessary to sterilize the surface of the body of the NEMATODES before the inoculation on the medium. The sterilization is conducted in a conventional method with a streptomycin aqueous solution, after an adequate number of the NEMATODES is centrifugally washed with sterilized water and condensed.

The incubation is conducted in an aerobic condition, aerating with a sterilized air, at 25° C. The amount of the aeration may be the minimum amount for the using container. The aeration may be stopped occasionally. Particularly, the aeration may not be conducted for 3 days after the inoculation of the fungus and the NEMATODES.

The pH is measured every two weeks, and if it is 6 or more, the pH of the medium is adjusted to slightly lower (pH: 5.0~5.2). If the NEMATODES coil themselves and begin to adhere onto the glass wall surface, the NEMATODES are washed out of the container and sifted on a 400 mesh sieve. A sponge is placed on a 100 mesh sieve, and underneath a 400 mesh sieve is extended for collecting the NEMATODES. The collected NEMATODES are preserved according to the above-described preservation method.

Next, explanation will be made of the agricultural application of the mass-produced NEMATODES according to the present invention. The NEMATODES can be applied widely in farming crops, for biological control of soil-borne diseases of vegetables, prevention of propagation of plant-parasitic injurious nematodes, or integrated control of soil-borne insect pests.

Control of Soil-borne Diseases

For example, in the soil containing *Rhizoctonia solani* AG-4, *Fusarium oxysporum* f. sp. *lagenariae*, Pythium sp., and/or *Phytophthora nicotiana* var. parasitica which are soil pathogenic fungi of cucumber damping-off, cucumbers do not germinate at all. If the soil is inoculated with preferably at most 400,000 NEMATODES, more preferably at most 200,000 NEMATODES per 1 liter soil and incubated about a week, the germination ratio of the cucumbers reaches 70–85% of the germination ratio in sterilized soil (neither containing soil pathogens nor the NEMATODES). Thus, the effect in control of soil-borne diseases is significantly large. It is surprising indeed that the germination ratio in coexistence of the soil pathogens is hardly recognized as compared with the germination ratio in the case where the NEMATODES are applied alone. If more than 400,000 NEMATODES per 1 liter soil are inoculated, the germination ratio will be rather decreased.

Further, in the soil containing plant pathogens, for example, cucumber damping-off pathogens and plant-parasitic nematodes such as Meloidogyne spp. or Pratylenchus spp., germination inhibition of cucumber seeds can be prevented with the NEMATODES. Namely, whereas the germination ratio of cucumbers is nil in the soil with damping-off pathogens, or the soil infested with the mixture of damping-off pathogens and Meloidogyne spp. or Pratylenchus spp., the germination inhibition is not seen when the soil containing the damping-off pathogens is admixed with about 200,000~500,000 NEMATODES, preferably 400,000 NEMATODES, per 1 liter soil and then sown with plant seeds. In the case where these soils are further admixed with the entomopathogenic nematode, *Steinernema carpocapsae*, in an amount of about 500,000~1,500,000, preferably about 1,000,000, per 1 m², the germination inhibition also does not occur at all. Examples of the above soil pathogens include *Rhizoctonia solani* AG-4, *Fusarium oxysporum* f. sp. *lagenariae*, Pythium sp. and *Phytophthora nicotiana* var. *parasitica*.

Furthermore, when the ternary system of damping-off pathogens, the NEMATODES and the entomopathogenic nematode are admixed with about 200 per 1 liter soil of, for example, at least one species of plant-parasitic nematodes selected from the group consisting of Meloidogyne spp. and Pratylenchus spp., the germination ratio is decreased from 100% to 80%. However, the height of the grown plants is comparable. Thus, the effect in eliminating the damages of insect pests by combination use of the NEMATODES with the beneficial nematode is remarkable.

Further, the fumigated and non-fumigated trial fields, each comprising a pathogen solely inoculated zone where the damping-off pathogen, *Rhizoctonia solani* AG-4, is inoculated and a mixed inoculated zone where a large quantity (for example, about $2 \times 10^8$) of the NEMATODES is admixed therewith, are provided. For example, when these trial fields are sown with spinach sprouted seeds, the germination ratio after 20 days is high in the pathogen solely inoculated zone in the non-fumigated trial field, and significantly low in the fumigated trial field, and 100% died within a week. Namely, in the fumigated field, the soil treatment with a chemical substance results in a drastic impoverishment of biota, wherefore injurious organisms rapidly recovers. On the other hand, in the mixed inoculated zones, inversely, the germination ratio is high in the fumigated trial field, and low in the non-fumigated trial field. This is conjectured to occur because the non-fumigated field is abundant in biota so that an interferential action between organisms is large. If the NEMATODES are applied to the soil which is thus chemical-treated, the effect in prevention of soil-borne diseases can be increased.

Suppression of Propagation of Plant-parasitic Nematode

The propagation of the plant-parasitic injurious nematodes can be suppressed by applying the mass-produced NEMATODES to the soil containing plant-parasitic injurious nematodes. The object of the present invention can be achieved by applying the NEMATODES in a quantity of 50~100 times the above plant-parasitic injurious nematodes. Examples of the plant-parasitic nematodes include at least one species selected from the group consisting of Neloidogyne spp. and Pratylenchus spp.

Integrated Control of Soil-borne Diseases and Insect Pests

For the soil containing both the pathogens and insect pests, an integrated control can be conducted by mixed inoculation of the entomopathogenic nematodes (*Steinernema carpocapsae*) with the NEMATODES. Further, with respect to the soil insect pests, common cutworm, *Spodoptera litura*, and turnip moth, *Agrotis segetum*, a remarkable effect of the present invention was confirmed, but this invention is not limited to them.

When the above soil insect pest is *Spodoptera litura*, the NEMATODES are preferably mixed with at least an equal amount of *Steinernema carpocapsae*, and when the soil insect pest is *Agrotis segetum*, the NEMATODES are preferably mixed with a substantially equal amount of *Steinernema carpocapsae*.

The process for mass production and long-term preservation and the method for utilizing the NEMATODES, according to the present invention will be explained in detail by way of examples hereinafter.

EXAMPLE 1

[Mass Production of Fungivorous Nematodes, *Aphelenchus avenae*, with a Solid Medium]

Beet pulp 10.0 g (wet weight) and Brewer's grains 10.0 g (wet weight) were mixed in a 500 ml glass container, and heat-sterilized in an autoclave at 120° C. for 30 min. After cooling, a solid medium having pH of 5.2 was obtained. The medium had a water content of 58% by weight. This medium was inoculated with a fungus, *Botrytis cinerea*, which had been axenically cultured, and incubated at 25°C.±1° C. for 3 days. Separately, 50 NEMATODES were soaked in a streptomycin 1,000 ppm solution for 30 minutes and washed with sterilized water 3 times, to sterilize the surface of the body. The medium in which the above fungus was propagated for 3 days was inoculated with the NEMATODES which had been sterilized their body surfaces, and incubated at the above constant temperature for 3 weeks. The container was lidded so as to prevent acari from entering but to allow the air to pass through. After incubation for 3 weeks, about 4,000,000 NEMATODES were obtained. Used tea leaves were not used, pH was raised to 6.5 after 3 weeks. However, according to this process, about 4,000,000 NEMATODES per 8.4g dry medium, i.e., 480,000,000 NEMATODES per 1 kg dry medium can be produced.

EXAMPLE 2

[Mass Production of Fungivorous Nematodes, *Aphelenchus avenae*, with an Artificial Liquid Medium]

A commercially available multiporous resin sponge (trade name: Everlight Piece) to be used for pillows or cushions was cut into strips 0.5 cm thick, about 1 cm wide and about 20 cm long, washed well with water and dried. The strips were used as substrates. A liquid medium was prepared with 600 g of potato, 60 g of dextrose or sucrose, and 3,000 ml of Sørensen's phosphate buffer solution (pH in the range of 5.2–5.5). The above sponge substrates were impregnated with the prepared liquid medium and introduced into a 5L-fermentor in an amount of 70 percent of the fermentor. After an excessive liquid was removed, sterilization was conducted in an autoclave at 120° C. for 60 minutes followed by natural cooling to provide an artificial liquid medium.

Then, 100~120 NEMATODES were washed with sterilized water 3 times by means of 1,500 rpm centrifugation, collected in a 50 ml cylinder and condensed to 5 ml. Adding 0.001% HIBITAT (chlorhexidine gluconate 5% (w/v) solution, Sumitomo Chemical Co.), the total volume was made to 30 ml and the NEMATODES were left to stand for 2 hours. During this period, aeration was conducted with a Pasteur pipette. Then, the NEMATODES were centrifugally washed with sterilized water 3 times and the liquid was condensed to 1 ml. Then, 9 ml of sterilized water containing 10 mg streptomycin was added to make the total volume 10 ml, immediately thereafter centrifugation was conducted for 2 minutes and supernatant liquid was removed. After this operation was repeated twice, centrifugal washing with sterilized water was conducted 3 times and the liquid was condensed to 0.5 ml or less. Thus, the NEMATODES to be inoculated whose body surface was strilized were prepared.

The fungus *Rhizoctonia solani* and the NEMATODES were simultaneously poured from a fungi-planting opening of the fermentor flange into the fermentor and incubated at a temperature of 250° C. Three days after the inoculation of the fungi and the NEMATODES, aeration was conducted with sterilized air. The aeration quantity was the minimum quantity of the using container (in this case, 0.5 1/min.) The aeration was stopped occasionally. The pH was measured every two weeks and if it was 6 or more, the pH was adjusted to slightly lower (pH: 5.0~5.2) with the Sørensen buffered solution.

At the time when the NEMATODES coiled themselves and began to adhere onto the glass wall surface (25 days after the commencement of the incubation), the NEMATODES were washed out of the container and sifted on a 400 mesh sieve. A sponge is placed on a 100 mesh sieve, and underneath a 400 mesh sieve is extended for collecting the NEMATODES. The NEMATODES were collected on the 400 mesh sieve and about $2 \times 10^8$ NEMATODES collected were preserved according to the above-described preservation method.

EXAMPLE 3

The food fungus for the NEMEATODES was *Botrytis cinerea*. The above Example 2 was repeated except that the NEMATODES were poured 2 days after inoculation of the fungus on the artificial medium, and $2 \sim 3 \times 10^8$ NEMATODES were obtained.

EXAMPLE 4
[Long-term Preservation of NEMATODES]

The NEMATODES obtained in the above Example 1 were collected and formed into a lump which was put in a (10 liter) glass desiccator cabinet and kept under constant temperature and humidity at around 25° C. and a relative humidity of 97%, for 2 days. The solution for use in the humidity control may be any solution as far as it does not generate a noxious gas. In this example, a glycerine solution or a saturated salt aqueous solution was used. If the humidity was gradually reduced to 86%, 76%, 50% and 30% in every two consecutive days, the NEMATODES contracted into almost a coiled shape and turned into a perfect anhydrobiotic condition in 10 days. The NEMATODES in this state were able to be preserved in the interior for a long period of time.

The examples described below relates to an invention with respect to an agricultural application of the NEMATODES that were mass-produced according to the process of the present invention.
[Control of Soil Pathogens According to the NEMATODES]

EXAMPLE 5
"Cucumber Germination Pot Test"

A mixed soil (water content: 50%) of 15 parts of sterilized sand soil and 1 part of vermiculite was put into a 300 ml polystyrol pot. With wheat bran media, fungi, *Rhizoctonia solani* AG-4, *Fusarium oxysporum* f. sp. *lagenariae*, *Pythium* sp., and *Phytophthora nicotiana* var. *parasitica* were cultured for two weeks. Each 1 g of medium containing the cultured fungi was inoculated the above mixed soil together with 10,000, 50,000 or 100,000 of the NEMATODES. The soil in the pot was mixed. The pot was closed and placed in dark at 25° C. for a week. Then, 4 grains per pot of sterilized cucumber seeds were sowed. Each procedure was repeated 10 times and a germination ratio was determined after 5 days. The results are shown in Table 1.

TABLE 1

Effect in application of *Aphelenchus avenae* against pathogens of cucumber damping-off [survival ratio of cucumber seedlings 14 days after sowing]

| | *Aphelenchus avenae*/300 ml soil | | | |
|---|---|---|---|---|
| Pathogens | Nil | 10,000 | 50,000 | 100,000 |
| None | 100.0 a | 79.3 b | 67.5 be | 43.2 c |
| *Rhizoctonia solani* AG-4 | 0 d | 69.5 be | 84.1 b | 51.0 f |
| *Fusarium oxysporum* f. sp. *lagenariae* | 0 d | 72.2 be | 77.6 bg | 52.4 f |
| *Pythium* sp. | 0 d | 76.7 bg | 80.0 b | 49.0 f |
| *Phytophthora nicotiana* var. *parasitica* | 0 d | 76.5 bg | 81.2 b | 54.7 f |

The survival ratio suffixed with the same alphabetical letter in the same column is not significantly different with the level of significance of 5%. (Explanation: for example, in the 100,000 NEMATODES inoculated zone, none of pathogens is 43.2% which is significantly different from the others, and the others are 49%~54% which are suffixed with f, that means, not significantly different.)

In this test, since the sterilized soil was used, it was seen that the germination ratio was lowered in the NEMATODE solely inoculated zone. Thus, the germination ratio was about 80% in the 10,000 NEMATODES inoculated zone, about 70% in the 50,000 NAMATODES inoculated zone and about 40% in the 100,000 NAMATODES inoculated zone. When the NEMATODES were inoculated together with the pathogens, the germination ratio was 70~80% in the 10,000 NEMATODES inoculated zone, 80~85% in the 50,000 NEMATODES inoculated zone and rather decreased to about 50% in the 100,000 NEMATODES inoculated zone. Considering that the germination ratio of the cucumbers was 0% with any pathogens in the zones only pathogens inoculated, the effect in application of the NEMATODES was quite clear. However, in this test, an appropriate quantity was 50,000 NEMATODES per pot. The propagation in the test tube of the NEMATODES used, Kyushu isolates, was the highest with *Rhizoctonia solani,* and very low with Fusarium and Pythium. However, the germination ratio of the cucumbers and the effect in control seen from the growing were not significantly different between the species of the pathogens. Further, the ratio of the NEMATODES propagated in the pot was 2.5~2.7 times the inoculated number (10,000 NEMATODES inoculated zone) which was not significantly different between the species of the pathogens.

EXAMPLE 6

"Cucumber Germination Pot Test"

A 500 ml sterilized sand soil was put into a polystyrol pot. With a wheat bran medium, fungus *Rhizoctonia solani* AG-4 was cultured in the same manner as Example 5. Each 1 g of the wheat bran medium containing the cultured fungi and 50,000, 100,000, 200,000, 500,000 or 1,000,000 of the NEMATODES were mixed with the above sterilized sand soil. The mixture having a water content of about 35% was sealed tightly and placed in dark at 25° C. for 2 weeks. Then, three grains per pot of cucumber seeds were sowed. One procedure was repeated 10 times. The germination ratios after 5 days and growing conditions after 16 days were examined. The results are shown in Table 2.

TABLE 2

Effect of fungivorous nematodes, *Aphelenchus avenae*, in control of cucumber damping-off, *Rhizoctonia solani* AG-4
[survival ratio of cucumbers 16 days after sowing]

| Test soil | Survival ratio of cucumbers (18–23° C.) |
|---|---|
| Cucumber damping-off pathogen *R. solani* AG-4 (1 g medium) solely inoculated | 13.3 a |
| *R. solani* + *A. avenae*: 5 × 10$^4$/500 ml soil | 86.7 bc |
| *R. solani* + *A. avenae*: 1 × 10$^5$/500 ml soil | 86.7 bc |
| *R. solani* + *A. avenae*: 2 × 10$^5$/500 ml soil | 80.0 bc |
| *R. solani* + *A. avenae*: 5 × 10$^5$/500 ml soil | 66.7 b |

TABLE 2-continued

Effect of fungivorous nematodes, *Aphelenchus avenae*, in control of cucumber damping-off, *Rhizoctonia solani* AG-4
[survival ratio of cucumbers 16 days after sowing]

| Test soil | Survival ratio of cucumbers (18–23° C.) |
|---|---|
| *R. solani* + *A. avenae*: 1 × 10$^6$/500 ml soil | 73.3 c |
| None + none | 100.0 c |

The same alphabetical letter shows no significant difference by $\chi^2$ test (=5%) of living/dead.

In this test, since a nematode solely inoculated zone was not provided, damages caused by the nematodes themselves are not known. However, the effect of application of the nematodes in the control of damping-off is obviously shown. Namely, in the case of inoculation with a pathogen only, the germination ratio was 13.3%, while in the 50,000 NEMATODES inoculation zone, the germination ratio was 86.7% and thereafter the growth was normal. However, when the inoculation number was more than 200,000, the germination ratio was gradually decreased and when 500,000 NEMATODES were inoculated, the germination ratio was decreased to 66.7%. This is conjectured to be germination inhibition caused by the nematodes themselves. In the zone where neither the NEMATODES nor pathogens were inoculated, the germination ratio was naturally 100% [Ishibashi, N. (1993) Integrated control of insect pests by *Steiner nema carpocapasae.* In. "Nematodes and the Biological Control of Insect Pests" (Bedding, R., Akhurst, R. and Kaya H. eds.), CSIRO, East Melbourne, 105–113.].

EXAMPLE 7

[Pot Test for Control Cucumber Damping-off *Rhizoctonia solani* (combination test of root-knot nematode with entomopathogenic nematode)]

As a container, a 500 ml unglazed pot was used. To a pot of sterilized soil, a damping-off pathogen, *Rhizoctonia solani* AG-4, was introduced together with 1 g of a wheat bran which cultured *R. solani* AG-4. Then, 100 of sweet potato root-knot nematodes, 200,000 of the NEMATODES and 500,000 of entomopathogenic nematodes, *Steinernema carpocapsae,* were treated in the combination shown in Table 3 below.

TABLE 3

Combined inoculation test of fungivorous nematodes (*A. avenae*), entomopathogenic nematodes (*Steinernema carpocapsae*) and plant-parasitic nematodes (*Meloidogynae incognita*) (500 ml soil pot, cucumber survival ratio and height of the grown plants 13 days after sowing)

| Damping-off pathogen | + | Fungivorous nematode | + | Entomopathogenic nematode | + | Plant-parasitic nematode | Survival ratio | Height of grown plant (cm) |
|---|---|---|---|---|---|---|---|---|
| 1 g wheat bran medium | + | 0 | + | 0 | + | 0 | 0a | — |
| ditto | + | 0 | + | 0 | + | 100 | 0a | — |
| ditto | + | 2 × 10$^5$ | + | 0 | + | 0 | 100b | 23.1a |
| ditto | + | 2 × 10$^5$ | + | 5 × 10$^5$ | + | 0 | 100b | 26.3b |
| ditto | + | 2 × 10$^5$ | + | 5 × 10$^5$ | + | 100 | 80c | 25.7b |
| 0 | + | 0 | + | 0 | + | 0 | 100b | 26.3b |

With respect to both the survival ratio and the height of the grown plants, the numerical values suffixed with the same alphabetical letter are not significantly different. (p ≦ 0.05)

The water content of the soil was 50% and the number of repetition was 10. Then, 2 weeks after the treatment and placed in dark at 25° C., 4 grains of cucumber seeds were sown. It was transferred to a glass house, the survival ratio and the height of the grown plants were determined. The results are shown in Table 3. In the zones of only the damping-off pathogens and the mix-inoculated zone of the damping-off pathogens with the root-knot nematodes, the cucumber germination ratio was 0%. In the mix-inoculated zone of even 200,000 NEMATODES with the damping-off pathogens, the germination inhibition was not seen in the case of this test. However, the height of the grown plants was a little lower than the control zone (no inoculation zone). When the entomopathogenic nematodes were mixed, the germination ratio was 100% and the height of the grown plants was not significantly different from the control zone.

In the case where those three were mixed with the root-knot nematodes, the germination ratio was decreased to 80% but the height of the grown plants was not significantly different. Though the entomopathogenic nematodes are applied in the control of insect pests, they can be applied in combination with the NEMATODES for the purpose of simultaneous control of soil-borne diseases and insect pests. From this test, it was found that the combination of beneficial nematodes does not impair the effective performance of the NEMATODES and rather eliminates the damages caused by the NEMATODES. Similar results were also obtained in many experiments conducted thenceforth (Ishibashi, N., and Choi, D-R. (1991) Biological control of soil pests by mixed application of etomopathogenic and fungivorous nematodes. J. Nematol. 23: 175–181).

EXAMPLE 8
[Small Scale Field Test of Spinach Damping-off]

Test fields which were treated and non-treated with 15L/10a of a fumigant TERON II (the trade name of 1,3-dichloropropene, active ingredient: 98%) 6 months before in the campus site of the Saga University were used. In the middle of September, the NEMATODES were propagated by feeding *Botrytis cinerea* in a beet pulp medium of 6 m$^2$/zone. On the other hand, a damping-off pathogen, *Rhizoctonia solani* AG-4, was propagated in a wheat bran medium. The above damping-off pathogens with 40 g of the medium were mixed or non-mixed (damping-off pathogen only) with NEMATODES with 4 kg of medium (about 200,000,000 NEMATODES). The mixture was laid over the whole surface of the test zone and mixed with the soil. 3 repetitions made one treatment and after laying 1 week, spinach sprouting seedlings were sown (2 ridges). 20 days after the sowing, the growth was examined. The results are shown in Table 4.

TABLE 4

Effect of fungivorous nematodes, *Aphelenchus avenae*, in control of spinach damping-off pathogen, *Rhizoctonia solani* AG-4 (6 m$^2$/zone small scale field test).
Test zone was treated or non-treated with a fumigant TERON II (15 liter/10 a) 6 months before.

| Test zone | Spinach survival ratio (20 days after sowing) | |
|---|---|---|
| | Treated with TERON II | Non-treated |
| *R. solani* 40 g wheat bran medium | 5a | 28b |
| *R. solani* 40 g wheat bran medium + | 84a | 78b |
| *A. avenae* (beet pulp medium 3 kg) | | |
| Non-treated (medium only) | 100a | 100a |

As to the spinach, sprouting seedlings were sown. The alphabitical letter suffixed to the numerical letter is to compare between TERON II treated and non-treated zones (P = 0.05).

The germination ratio of the spinach sown with the pathogens only was high (28%) in the fumigant non-treated zone and significantly low (5% level) (germination ratio: 5%) in the fumigant treated zone. When the NEMATODES were applied, the germination ratio was high (84%) in the fumigated zone and low (78%) in the non-treated zone (these values were significantly different with the level of significance of 5%). It is considered that the soil in the non-treated zone has an abundant biota to cause more interferential actions between organisms than the soil of the treated zone. The spinach in the pathogen solely inoculated zone grew very badly. Particularly in the fumigated zone, 100% died within 1 week after examination. A soil treatment with chemical substances will result in a drastic indigence of biota and in its turn bring about a rapid recovery of injurious organisms. On the other hand, if the NEMATODES are applied in such soil, it is expected that the effect in prevention of soil-borne diseases will be further intensified [Ishibashi, N. (1993) Integrated control of insect pests by *Steinernema carpocapsae,* In. "Nematodes and the Biological Control of Insect Pests" (Bedding, R., Akhurst, R. and Kaya H. eds.), CSIRO, East Melbourne, 105–113.]

EXAMPLE 9
[Propagation Suppression of Plant-parasitic Nematodes by the NEMATODE]

Plant-parasitic nematodes, such as root-knot nematodes or root-lesion nematodes were inoculated simultaneously with the NEMATODES in 100 times density on an agar. The root invasion ratios of the plant-parasitic nematodes were 1–2% of the case of the plant-parasitic nematodes alone. Alternatively, a pot test using sterilized soil was conducted in that the NEMATODES were inoculated one day before inoculation of the plant-parasitic nematodes and that the invasion ratio of the plant-parasitic nematodes was decreased to 20% or less. However, in non-sterilized soil, it was not significantly different from the plant-parasitic nematode solely inoculated soil. On the other hand, the invasion ratio of the non-sterilized soil inoculated solely with the plant-parasitic nematodes was decreased to 30% or less of the sterilized soil inoculated solely with the plant-parasitic nematodes. In the natural world, particularly where many varieties of organisms coexist, the mechanism is not built for only pathogens to dominate. Therefore, it has been found that if the NEMATODES are applied to prevent the soil biota from deterioration by application of chemicals, it can effectively suppress a rapid recovery of injurious nematodes.

EXAMPLE 10
[Integrated Control of Soil-borne Pathogens and Insect Pests by Simultaneous Application with Entomopathogenic Nematodes]

It has been already found that when the NEMATODES are inoculated in combination with pathogens even in the sterilized soil, it will not damage the plants. If it is inoculated simultaneously with the entomopathogenic nematodes Steinernema, the plants are not damaged. For example, cucumbers germinate earlier and the germination ratio is higher rather than the NEMATODE solely inoculated zone. In combination application, inversely, in order to confirm the control effect of entomopathogenic nematodes against insect pests, several tests were repeated. An example of the test results is shown in Table 5.

TABLE 5

Effect of mixed application of fungivorous nematodes (*Aphelenchus avenae*) and entomopathogenic nematodes (*Steinernema carpocapsae*) on control of common cutworm (*Spodoptera litura*) and turnip moths (*Agrotis segetum*)

| | | | | Mortality ratio | | | | | |
|---|---|---|---|---|---|---|---|---|---|
| Mix ratio | | | S. litura | | | A. segetum | | | |
| S. carpocapsae | + | A. avenae | 48 hr | 72 hr | 96 hr | 48 hr | 72 hr | 96 hr | 120 hr |
| 0 | + | 0 | 0a | 0a | 0a | 0a | 0a | 0a | 0a |
| 0 | + | 5,000 | 0a | 0a | 0a | 0a | 0a | 0a | 0a |
| 50 | + | 0 | 85b | 95a | 100b | 50b | 80d | 90c | 90c |
| 50 | + | 50 | 95b | 100c | | 40b | 60cd | 80c | 90c |
| 50 | + | 500 | 95b | 100c | | 10a | 40bc | 60bc | 60bc |
| 50 | + | 5,000 | 95b | 100c | | 0a | 20b | 40b | 60bc |

The mortality ratio suffixed with the same alphabetical letter in the same column is not significantly different with the level of significance of 5% by $X^2$ test.

As apparent from Table 5, the conclusion has reached that against the larvae of the turnip moths which are the insect pests inherently having a fairly resistance to the steinernematid nematodes, when the NEMATODES are applied extremely more than the Steinernema, the Steinernema further decreases its insecticdal ability, but there will be little problem against the common cutworm or the like. With a view to the future, it can be expected that the NEMATODES are compatible with the beneficial nematodes such as Steinernema or the like [Ishibashi, N. (1993) Integrated control of insect pests by *Steinernema carpocapsae*. In. "Nematodes and the Biological Control of Insect Pests" (Bedding, R., Akhurst, R. and Kaya H. eds.), CSIRO, East Melbourne, 105–113.].

The meritorious effects of the present invention are as follows:

1. Fungivorous nematode, *Aphelenchus avenae*, can be mass-produced and a long-term preservation method of the mass-produced NEMATODES has been established. Moreover, deterioration of the NEMATODES owing to subculturing can be prevented. Therefore, the biological control by the NEMATODES of soil-borne diseases and insect pests in farming crops can be effectively utilized in practical agriculture.
2. Furthermore, since a propagation suppression method of soil pests and plant-parasitic nematodes for farming crops has been established utilizing the NEMATODES, it largely contributes to improvement of the yield and quality of the farming crops. Conclusively, the NEMATODES do not treat disease-suffering plants but are prophylactically applied and a remarkable effect is expected. Further, the NEMATODES should be applied in a proper quantity. An application of a more quantity than that rather decreases the effect.
3. The biological control of the soil-borne diseases of farming crops by utilizing the NEMATODES is not accompanied with environmental pollution or disruption owing to chemicals. Since the industrial wastes are effectively utilized in mass-production of the NEMATODES, it can contribute to cleaning of the environment.

What is claimed is:

1. A process for longterm preservation of fungivorous nematodes comprising
   a) mass-producing fungivorous nematodes by a method comprising sequentially,
      i) heat-sterlizing an artificial liquid medium comprising starch, dextrose or sucrose a phosphate buffer, and a multiporous substrate which is impregnated with said liquid medium; wherein said multiporous solid substrate is a spongy material selected from the group consisting of a microporous resins sponges, fiber linters, and fabrics;
      ii) inoculating said solid medium with a host fungus for at least one species of fungivorous nematodes;
      iii) surface-sterlizing fungivorous nematodes of said at least one species, and inoculating said liquid medium with the sterilized nematodes concurrently with, or following, said step of inoculating with said host fungus; and
      iv) incubating said fungivorous nematodes and fungus so as to mass-produce said nematodes;
   b) forming a lump comprising said mass-produced nematodes, and maintaining said lump at 20–25° C. for 8–12 days under aerobic conditions during which relative humidity is reduced in a stepwise manner from 97–100% to 25–40%, and the fungivorous nematodes are dessicated to an anhydrobiotic condition.

2. The process of claim 1, wherein said liquid medium is a Sorensen's phosphate buffer solution containing 150–250 g/l of starch and 15–25 g/l of dextrose or sucrose.

3. The process of claim 1, wherein said incubation is conducted by maintaining pH of the artificial liquid medium in a range of 5–6 during the cultivation.

4. The process of claim 1, wherein said steps for mass-producing fungivorous nematodes further comprise serial stepwise subculturing of the fungivorous nematodes with host fungi in artificial liquid medium comprising starch, dextrose or sucrose, a phosphate buffer, and a multiporous solid substrate which is impregnated with said liquid medium; wherein said multiporous solid substrate is a spongy material selected from the group consisting of a microporous resins, sponges, fiber linters, and fabrics:

wherein the species of host fungi in every stage of sub-culturing is different from the species of host fungi in the preceding stage, and wherein a non-pathogenic fungus is used in a final incubation stage.

5. The process of claim 4, wherein said different species of the host fungi are selected from *Botrytis cinerea, Rhizoctonia solani,* Pythium, Virticillium and Fusarium, and in the final incubation stage *Botrytis cinerea* is used.

6. The process of claim 1 wherein said microporous resins are selected from the group consisting of foamed polyurethanes and microporous polyvinyl formal resins.

7. The process of claim 1 wherein said sponges are selected from the group consisting of sponges of animal origin and sponges of vegetable origin.

8. The process of claim 1 wherein said fiber linters are selected from the group consisting of organic fiber linters and inorganic fiber linters.

9. The process of claim 1 wherein said fabrics are selected from the group consisting of woven fabrics, non-woven fabrics, and knitted fabrics.

10. The process of claim 4 wherein said microporous resins used in subculturing the fungivorous nematodes are selected from the group consisting of foamed polyurethanes and microporous polyvinyl formal resins.

11. The process of claim 4 wherein said sponges used in subculturing the fungivorous nematodes are selected from the group consisting of sponges of animal origin and sponges of vegetable origin.

12. The process of claim 4 wherein said fiber linters used in subculturing the fungivorous nematodes are selected from the group consisting of organic fiber linters and inorganic fiber linters.

13. The process of claim 4 wherein said fabrics used in subculturing the fungivorous nematodes are selected from the group consisting of woven fabrics, non-woven fabrics, and knitted fabrics.

* * * * *